(12) United States Patent
Yang et al.

(10) Patent No.: US 6,869,592 B1
(45) Date of Patent: Mar. 22, 2005

(54) METHOD AND ANTIBODY FOR IMAGING LUNG CANCER

(75) Inventors: Fei Yang, San Diego, CA (US); Yongming Sun, San Jose, CA (US); Herve Recipon, San Francisco, CA (US); Roberto A. Macina, San Jose, CA (US)

(73) Assignee: diaDexus, Inc., South San Francisco, CA (US)

( * ) Notice: Subject to any disclaimer, the term of this patent is extended or adjusted under 35 U.S.C. 154(b) by 0 days.

(21) Appl. No.: 09/762,028

(22) PCT Filed: Jul. 19, 1999

(86) PCT No.: PCT/US99/16247

§ 371 (c)(1),
(2), (4) Date: May 10, 2001

(87) PCT Pub. No.: WO00/08206

PCT Pub. Date: Feb. 17, 2000

Related U.S. Application Data

(60) Provisional application No. 60/095,233, filed on Aug. 4, 1998.

(51) Int. Cl.[7] .................... A61K 49/00; A61K 39/395; G01N 33/53; C12P 21/08
(52) U.S. Cl. .................... 424/9.34; 424/9.1; 424/9.341; 424/9.6; 424/142.1; 424/155.1; 424/130.1; 435/7.1; 435/7.21; 435/7.23; 530/388.1; 530/388.15; 530/389.1; 530/389.7; 530/388.8; 530/350; 536/23.5
(58) Field of Search .................. 424/9.34, 9.1, 424/9.341, 9.6, 142.1, 155.1, 130.1; 435/7.1, 7.21, 7.23; 530/388.1, 388.15, 389.1, 389.7, 388.8, 350; 536/23.5

(56) References Cited

U.S. PATENT DOCUMENTS 5,589,579 A   12/1996   Torczynski et al.

FOREIGN PATENT DOCUMENTS

| EP | 0 695 760 A1 | 5/1994 |
|----|--------------|--------|
| WO | WO 98/20143 | 5/1998 |
| WO | WO 98/20143 A1 | 5/1998 |
| WO | WO 00/08206 A1 | 2/2000 |
| WO | WO 00/78953 A2 | 12/2000 |
| WO | WO 01/22920 A2 | 4/2001 |
| WO | WO 01/64835 A2 | 9/2001 |
| WO | WO 02/10390 A2 | 2/2002 |

OTHER PUBLICATIONS

Kerlavage et al. National Center for Biotechnology Information, National Library of Medicine, NIH (Bethesda, MD, USA), GenBank Accession No. AA324584, Apr. 20, 1997.*

* cited by examiner

Primary Examiner—Carla J. Myers
(74) Attorney, Agent, or Firm—Licata & Tyrrell P.C.

(57) ABSTRACT

The present invention provides new methods for detecting, diagnosing, monitoring, staging, prognosticating, imaging and treating lung cancer.

3 Claims, No Drawings

METHOD AND ANTIBODY FOR IMAGING LUNG CANCER

This application is the National Stage of International Application PCT/US99/16247, filed Jul. 19, 1999, which claims the benefit of U.S. Provisional Application No. 60/095,233, filed Aug. 4,1998.

FIELD OF THE INVENTION

This invention relates, in part, to newly developed assays for detecting, diagnosing, monitoring, staging, prognosticating, imaging and treating cancers, particularly lung cancer.

BACKGROUND OF THE INVENTION

Lung cancer is the second most prevalent type of cancer for both men and women in the United States and is the most common cause of cancer death in both sexes. Lung cancer can result from a primary tumor originating in the lung or a secondary tumor which has spread from another organ such as the bowel or breast. Primary lung cancer is divided into three main types; small cell lung cancer; non-small cell lung cancer; and mesothelioma. Small cell lung cancer is also called "Oat Cell" lung cancer because the cancer cells are a distinctive oat shape. There are three types of non-small cell lung cancer. These are grouped together because they behave in a similar way and respond to treatment differently to small cell lung cancer. The three types are squamous cell carcinoma, adenocarcinoma, and large cell carcinoma. Squamous cell cancer is the most common type of lung cancer. It develops from the cells that line the airways. Adenocarcinoma also develops from the cells that line the airways. However, adenocarcinoma develops from a particular type of cell that produces mucus (phlegm). Large cell lung cancer has been thus named because the cells look large and rounded when they are viewed under a microscope. Mesothelioma is a rare type of cancer which affects the covering of the lung called the pleura. Mesothelioma is often caused by exposure to asbestos.

Secondary lung cancer is cancer that has started somewhere else in the body (for example, the breast or bowel) and spread to the lungs. Choice of treatment for secondary lung cancer depends on where the cancer started. In other words, cancer that has spread from the breast should respond to breast cancer treatments and cancer that has spread from the bowel should respond to bowel cancer treatments.

The stage of a cancer indicates how far a cancer has spread. Staging is important because treatment is often decided according to the stage of a cancer. The staging is different for non-small cell and for small cell cancers of the lung.

Non-small cell cancer can be divided into four stages. Stage I is very localized cancer with no cancer in the lymph nodes. Stage II cancer has spread to the lymph nodes at the top of the affected lung. Stage III cancer has spread near to where the cancer started. This can be to the chest wall, the covering of the lung (pleura), the middle of the chest (mediastinum) or other lymph nodes. Stage IV cancer has spread to another part of the body.

Since small cell lung cancer can spreads quite early in development of the disease, small cell lung cancers are divided into only two groups. These are: limited disease, that is cancer that can only be seen in one lung and in nearby lymph nodes; and extensive disease, that is cancer that has spread outside the lung to the chest or to other parts of the body. Further, even if spreading is not apparent on the scans, it is likely that some cancer cells will have broken away and traveled through the bloodstream or lymph system. To be safe, it is therefore preferred to treat small cell lung cancers as if they have spread, whether or not secondary cancer is visible. Because surgery is not typically used to treat small cell cancer, except in very early cases, the staging is not as critical as it is with some other types of cancer. Chemotherapy with or without radiotherapy is often employed. The scans and tests done at first will be used later to see how well a patient is responding to treatment.

WO 98/56951 (published Dec. 17, 1998) discloses a set of contiguous and partially overlapping cDNA sequences and polypeptides encoded thereby, designated as LS170. These sequences are suggested to be useful in detecting, diagnosing, staging, monitoring, prognosticating, in vivo imaging, preventing or treating, and determining the predisposition of an individual to disease and conditions of the lung, such as lung cancer. The LS170-specific polynucleotide is taught to have at least 50% identity with a polynucleotide selected from the group consisting of SEQ ID NO:1–9 as disclosed in WO 98/56951. SEQ ID NO:1 taught in WO 98/56951 overlaps with an LSG, SEQ ID NO: 4, used in the instant invention.

In the present invention methods are provided for detecting, diagnosing, monitoring, staging, prognosticating, in vivo imaging and treating lung cancer via five (5) Lung Specific Genes (LSG). The five LSGs refer, among other things, to native proteins expressed by the genes comprising the polynucleotide sequences of any of SEQ ID NO: 1, 2, 3, 4, or 5. In the alternative, what is meant by the five LSGs as used herein, means the native mRNAs encoded by the genes comprising any of the polynucleotide sequences of SEQ ID NO: 1, 2, 3, 4, or 5 or it can refer to the actual genes 25 comprising any of the polynucleotide sequences of SEQ ID NO: 1, 2, 3, 4, or 5.

Procedures used for detecting, diagnosing, monitoring, staging, and prognosticating lung cancer are of critical importance to the outcome of the patient. For example, patients diagnosed with early lung cancer generally have a much greater five-year survival rate as compared to the survival rate for patients diagnosed with distant metastasized lung cancer. New diagnostic methods which are more sensitive and specific for detecting early lung cancer are clearly needed.

Lung cancer patients are closely monitored following initial therapy and during adjuvant therapy to determine response to therapy and to detect persistent or recurrent disease of metastasis. There is clearly a need for a lung cancer marker which is more sensitive and specific in detecting lung cancer, its recurrence and progression.

Another important step in managing lung cancer is to determine the stage of the patient's disease. Stage determination has potential prognostic value and provides criteria for designing optimal therapy. Generally, pathological staging of lung cancer is preferable over clinical staging because the former gives a more accurate prognosis. However, clinical staging would be preferred were it at least as accurate as pathological staging because it does not depend on an invasive procedure to obtain tissue for pathological evaluation. Staging of lung cancer would be improved by detecting new markers in cells, tissues, or bodily fluids which could differentiate between different stages of invasion.

Other objects, features, advantages and aspects of the present invention will become apparent to those of skill in the art from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

SUMMARY OF THE INVENTION

Toward these ends, and others, it is an object of the present invention to provide a method for diagnosing the presence of lung cancer by analyzing for changes in levels of LSG in cells, tissues or bodily fluids compared with levels of LSG in preferably the same cells, tissues, or bodily fluid type of a normal human control, wherein an increase in levels of LSG in the patient versus normal human control is associated with lung cancer.

Further provided is a method of diagnosing metastatic lung cancer in a patient having such cancer which is not known to have metastasized by identifying a human patient suspected of having lung cancer that has metastasized; analyzing a sample of cells, tissues, or bodily fluid from such patient for LSG; comparing the LSG levels in such cells, tissues, or bodily fluid with levels of LSG in preferably the same cells, tissues, or bodily fluid type of a normal human control, wherein an increase in LSG levels in the patient versus the normal human control is associated with a cancer which has metastasized.

Also provided by the invention is a method of staging lung cancer in a human which has such cancer by identifying a human patient having such cancer; analyzing a sample of cells, tissues, or bodily fluid from such patient for LSG; comparing LSG levels in such cells, tissues, or bodily fluid with levels of LSG in preferably the same cells, tissues, or bodily fluid type of a normal human control sample, wherein an increase in LSG levels in the patient versus the normal human control is associated with a cancer which is progressing and a decrease in the levels of LSG is associated with a cancer which is regressing or in remission.

Further provided is a method of monitoring lung cancer in a human having such cancer for the onset of metastasis. The method comprises identifying a human patient having such cancer that is not known to have metastasized; periodically analyzing a sample of cells, tissues, or bodily fluid from such patient for LSG; comparing the LSG levels in such cells, tissue, or bodily fluid with levels of LSG in preferably the same cells, tissues, or bodily fluid type of a normal human control sample, wherein an increase in LSG levels in the patient versus the normal human control is associated with a cancer which has metastasized.

Further provided is a method of monitoring the change in stage of lung cancer in a human having such cancer by looking at levels of LSG in a human having such cancer. The method comprises identifying a human patient having such cancer; periodically analyzing a sample of cells, tissues, or bodily fluid from such patient for LSG; comparing the LSG levels in such cells, tissue, or bodily fluid with levels of LSG in preferably the same cells, tissues, or bodily fluid type of a normal human control sample, wherein an increase in LSG levels in the patient versus the normal human control is associated with a cancer which is progressing and a decrease in the levels of LSG is associated with a cancer which is regressing or in remission.

Further provided are antibodies against the LSGs or fragments of such antibodies which can be used to detect or image localization of the LSGs in a patient for the purpose of detecting or diagnosing a disease or condition. Such antibodies can be polyclonal or monoclonal, or prepared by molecular biology techniques. The term "antibody", as used herein and throughout the instant specification is also meant to include aptamers and single-stranded oligonucleotides such as those derived from an in vitro evolution protocol referred to as SELEX and well known to those skilled in the art.

Antibodies can be labeled with a variety of detectable labels including, but not limited to, radioisotopes and paramagnetic metals. These antibodies or fragments thereof can also be used as therapeutic agents in the treatment of diseases characterized by expression of a LSG. In therapeutic applications, the antibody can be used without or with derivatization to a cytotoxic agent such as a radioisotope, enzyme, toxin, drug or a prodrug.

Other objects, features, advantages and aspects of the present invention will become apparent to those of skill in the art from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

DESCRIPTION OF THE INVENTION

The present invention relates to diagnostic assays and methods, both quantitative and qualitative for detecting, diagnosing, monitoring, staging, prognosticating, in vivo imaging and treating cancers by comparing levels of LSG with those of LSG in a normal human control. What is meant by levels of LSG as used herein, means levels of the native protein expressed by the gene comprising the polynucleotide sequence of any of SEQ ID NO: 1, 2, 3, 4, or 5. In the alternative, what is meant by levels of LSG as used herein, means levels of the native mRNA encoded by the gene comprising any of the polynucleotide sequences of SEQ ID NO: 1, 2, 3, 4, or 5 or levels of the gene comprising any of the polynucleotide sequence of SEQ ID NO: 1, 2, 3, 4, or 5. Such levels are preferably measured in at least one of, cells, tissues and/or bodily fluids, including determination of normal and abnormal levels. Thus, for instance, a diagnostic assay in accordance with the invention for diagnosing overexpression of LSG protein compared to normal control bodily fluids, cells, or tissue samples may be used to diagnose the presence of cancers, including lung cancer. Any of the five LSGs may be measured alone in the methods of the invention, or all together or any combination of the five.

All the methods of the present invention may optionally include measuring the levels of other cancer markers as well as LSG. Other cancer markers, in addition to LSG, useful in the present invention will depend on the cancer being tested and are known to those of skill in the art.

Diagnostic Assays

The present invention provides methods for diagnosing the presence of lung cancer by analyzing for changes in levels of LSG in cells, tissues or bodily fluids compared with levels of LSG in cells, tissues or bodily fluids of preferably the same type from a normal human control, wherein an increase in levels of LSG in the patient versus the normal human control is associated with the presence of lung cancer.

Without limiting the instant invention, typically, for a quantitative diagnostic assay a positive result indicating the patient being tested has cancer is one in which cells, tissues, or bodily fluid levels of the cancer marker, such as LSG, are at least two times higher, and most preferable are at least five times higher, than in preferably the same cells, tissues, or bodily fluid of a normal human control.

The present invention also provides a method of diagnosing metastatic lung cancer in a patient having lung cancer which has not yet metastasized for the onset of metastasis. In the method of the present invention, a human cancer patient suspected of having lung cancer which may have metastasized (but which was not previously known to have metastasized) is identified. This is accomplished by a variety of means known to those of skill in the art. For example, in the case of lung cancer, patients are typically diagnosed with lung cancer following traditional detection methods.

In the present invention, determining the presence of LSG level in cells, tissues, or bodily fluid, is particularly useful for discriminating between lung cancer which has not metastasized and lung cancer which has metastasized. Existing techniques have difficulty discriminating between lung cancer which has metastasized and lung cancer which has not metastasized and proper treatment selection is often dependent upon such knowledge.

In the present invention, the cancer marker level measured in such cells, tissues, or bodily fluid is LSG, and is compared with levels of LSG in preferably the same cells, tissue, or bodily fluid type of a normal human control. That is, if the cancer marker being observed is just LSG in serum, this level is preferably compared with the level of LSG in serum of a normal human patient. An increase in the LSG in the patient versus the normal human control is associated with lung cancer which has metastasized.

Without limiting the instant invention, typically, for a quantitative diagnostic assay a positive result indicating the cancer in the patient being tested or monitored has metastasized is one in which cells, tissues, or bodily fluid levels of the cancer marker, such as LSG, are at least two times higher, and more preferably are at least five times higher, than in preferably the same cells, tissues, or bodily, fluid of a normal patient.

Normal human control as used herein includes a human patient without cancer and/or non cancerous samples from the patient; in the methods for diagnosing metastasis or monitoring for metastasis, normal human control preferably includes samples from a human patient that is determined by reliable methods to have lung cancer which has not metastasized such as samples from the same patient prior to metastasis.

Staging

The invention also provides a method of staging lung cancer in a human patient.

The method comprises identifying a human patient having such cancer and analyzing a sample of cells, tissues, or bodily fluid from such patient for LSG. The measured LSG levels are then compared to levels of LSG in preferably the same cells, tissues, or bodily fluid type of a normal human control sample, wherein an increase in LSG levels in the patient versus the normal human control is associated with a cancer which is progressing and a decrease in the levels of LSG is associated with a cancer which is regressing or in remission.

Monitoring

Further provided is a method of monitoring lung cancer in a human having such cancer for the onset of metastasis. The method comprises identifying a human patient having such cancer that is not known to have metastasized; periodically analyzing a sample of cells, tissues, or bodily fluid from such patient for LSG; comparing the LSG levels in such cells, tissue, or bodily fluid with levels of LSG in preferably the same cells, tissues, or bodily fluid type of a normal human control sample, wherein an increase in LSG levels in the patient versus the normal human control is associated with a cancer which has metastasized.

Further provided by this inventions is a method of monitoring the change in stage of lung cancer in a human having such cancer. The method comprises identifying a human patient having such cancer; periodically analyzing a sample of cells, tissues, or bodily fluid from such patient for LSG; comparing the LSG levels in such cells, tissue, or bodily fluid with levels of LSG in preferably the same cells, tissues, or bodily fluid type of a normal human control sample, wherein an increase in LSG levels in the patient versus the normal human control is associated with a cancer which is progressing in stage and a decrease in the levels of LSG is associated with a cancer which is regressing in stage or in remission.

Monitoring such patient for onset of metastasis is periodic and preferably done on a quarterly basis. However, this may be more or less frequent depending on the cancer, the particular patient, and the stage of the cancer.

Assay Techniques

Assay techniques that can be used to determine levels of gene expression, such as LSG of the present invention, in a sample derived from a host are well-known to those of skill in the art. Such assay methods include radioimmunoassays, reverse transcriptase PCR (RT-PCR) assays, immunohistochemistry assays, in situ hybridization assays, competitive-binding assays, Western Blot analyses, ELISA assays and proteomic approaches. Among these, ELISAs are frequently preferred to diagnose a gene's expressed protein in biological fluids.

An ELISA assay initially comprises preparing an antibody, if not readily available from a commercial source, specific to LSG, preferably a monoclonal antibody. In addition a reporter antibody generally is prepared which binds specifically to LSG. The reporter antibody is attached to a detectable reagent such as radioactive, fluorescent or enzymatic reagent, for example horseradish peroxidase enzyme or alkaline phosphatase.

To carry out the ELISA, antibody specific to LSG is incubated on a solid support, e.g., a polystyrene dish, that binds the antibody. Any free protein binding sites on the dish are then covered by incubating with a non-specific protein such as bovine serum albumin. Next, the sample to be analyzed is incubated in the dish, during which time LSG binds to the specific antibody attached to the polystyrene dish. Unbound sample is washed out with buffer. A reporter antibody specifically directed to LSG and linked to horseradish peroxidase is placed in the dish resulting in binding of the reporter antibody to any monoclonal antibody bound to LSG. Unattached reporter antibody is then washed out. Reagents for peroxidase activity, including a calorimetric substrate are then added to the dish. Immobilized peroxidase, linked to LSG antibodies, produces a colored reaction product. The amount of color developed in a given time period is proportional to the amount of LSG protein present in the sample. Quantitative results typically are obtained by reference to a standard curve.

A competition assay may be employed wherein antibodies specific to LSG attached to a solid support and labeled LSG and a sample derived from the host are passed over the solid support and the amount of label detected attached to the solid support can be correlated to a quantity of LSG in the sample.

Nucleic acid methods may be used to detect LSG mRNA as a marker for lung cancer. Polymerase chain reaction (PCR) and other nucleic acid methods, such as ligase chain reaction (LCR) and nucleic acid sequence based amplification (NASABA), can be used to detect malignant cells for diagnosis and monitoring of various malignancies. For example, reverse-transcriptase PCR (RT-PCR) is a powerful technique which can be used to detect the presence of a specific mRNA population in a complex mixture of thousands of other mRNA species. In RT-PCR, an mRNA species is first reverse transcribed to complementary DNA (cDNA) with use of the enzyme reverse transcriptase; the cDNA is then amplified as in a standard PCR reaction. RT-PCR can thus reveal by amplification the presence of a single species of mRNA. Accordingly, if the mRNA is highly specific for the cell that produces it, RT-PCR can be used to identify the presence of a specific type of cell.

Hybridization to clones or oligonucleotides arrayed on a solid support (i.e., gridding) can be used to both detect the expression of and quantitate the level of expression of that gene. In this approach, a cDNA encoding the LSG gene is fixed to a substrate. The substrate may be of any suitable type including but not limited to glass, nitrocellulose, nylon or plastic. At least a portion of the DNA encoding the LSG gene is attached to the substrate and then incubated with the analyte, which may be RNA or a complementary DNA (cDNA) copy of the RNA, isolated from the tissue of interest. Hybridization between the substrate bound DNA and the analyte can be detected and quantitated by several means including but not limited to radioactive labeling or fluorescence labeling of the analyte or a secondary molecule designed to detect the hybrid. Quantitation of the level of gene expression can be done by comparison of the intensity of the signal from the analyte compared with that determined from known standards. The standards can be obtained by in vitro transcription of the target gene, quantitating the yield, and then using that material to generate a standard curve.

Of the proteomic approaches, 2D electrophoresis is a technique well known to those in the art Isolation of individual proteins from a sample such as serum is accomplished using sequential separation of proteins by different characteristics usually on polyacrylamide gels. First, proteins are separated by size using an electric current. The current acts uniformly on all proteins, so smaller proteins move farther on the gel than larger proteins. The second dimension applies a current perpendicular to the first and separates proteins not on the basis of size but on the specific electric charge carried by each protein. Since no two proteins with different sequences are identical on the basis of both size and charge, the result of a 2D separation is a square gel in which each protein occupies a unique spot. Analysis of the spots with chemical or antibody probes, or subsequent protein microsequencing can reveal the relative abundance of a given protein and the identity of the proteins in the sample.

The above tests can be carried out on samples derived from a variety of patients' cells, bodily fluids and/or tissue extracts (homogenates or solubilized tissue) such as from tissue biopsy and autopsy material. Bodily fluids useful in the present invention include blood, urine, saliva, or any other bodily secretion or derivative thereof. Blood can include whole blood, plasma, serum, or any derivative of blood.

In Vivo Antibody Use

Antibodies against LSG can also be used in vivo in patients with disease of the lung. Specifically, antibodies against an LSG can be injected into a patient suspected of having a disease of the lung for diagnostic and/or therapeutic purposes. The use of antibodies for in vivo diagnosis is well known in the art. For example, antibody-chelators labeled with Indium-111 have been described for use in the radio-immunoscintographic imaging of carcinoembryonic antigen expressing tumors (Sumerdon et al. Nucl. Med. Biol. 1990 17:247–254). In particular, these antibody-chelators have been used in detecting tumors in patients suspected of having recurrent colorectal cancer (Griffin et al. J. Clin. Onc. 1991 9:631–640). Antibodies with paramagnetic ions as labels for use in magnetic resonance imaging have also been described (Lauffer, R. B. Magnetic Resonance in Medicine 1991 22:339–342). Antibodies directed against LSGs can be used in a similar manner. Labeled antibodies against an LSG can be injected into patients suspected of having a disease of the lung such as lung cancer for the purpose of diagnosing or staging of the disease status of the patient. The label used will be selected in accordance with the imaging modality to be used. For example, radioactive labels such as Indium-111, Technetium-99m or Iodine-131 can be used for planar scans or single photon emission computed tomography (SPECT). Positron emitting labels such as Fluorine-19 can be used in positron emission tomography. Paramagnetic ions such as Gadlinium (III) or Manganese (II) can used in magnetic resonance imaging (MRI). Localization of the label within the lung or external to the lung permits determination of the spread of the disease The amount of label within the lung also allows determination of the presence or absence of cancer in the lung.

For patients diagnosed with lung cancer, injection of an antibody against an LSG can also have a therapeutic benefit. The antibody may exert its therapeutic effect alone. Alternatively, the antibody is conjugated to a cytotoxic agent such as a drug, toxin or radionuclide to enhance its therapeutic effect. Drug monoclonal antibodies have been described in the art for example by Garnett and Baldwin, Cancer Research 1986 46:2407–2412. The use of toxins conjugated to monoclonal antibodies for the therapy of various cancers has also been described by Pastan et al. Cell 1986 47:641–648). Yttrium-90 labeled monoclonal antibodies have, been described for maximization of dose delivered to the tumor while limiting toxicity to normal tissues (Goodwin and Meares Cancer Supplement 1997 80:2675–2680). Other cytotoxic radionuclides including, but not limited to Copper-67, Iodine-131 and Rhenium-186 can also be used for labeling of antibodies against LSGs.

Antibodies which can be used in these in vivo methods include both polyclonal and monoclonal antibodies and antibodies prepared via molecular biology techniques. Antibody fragments can also be used.

EXAMPLES

The present invention is further described by the following examples. The examples are provided solely to illustrate the invention by reference to specific embodiments. These exemplifications, while illustrating certain specific aspects of the invention, do not portray the limitations or circumscribe the scope of the disclosed invention.

Example 1

Searches were carried out and LSGs identified using the following Search Tools as part of the LIFESEQ database available from Incyte Pharmaceuticals, Palo Alto, Calif.:

Library Comparison (compares one library to one other library) allows the identification of clones expressed in tumor and absent or expressed at a lower level in normal tissue.

Subsetting is similar to library comparison but allows the identification of clones expressed in a pool of libraries and absent or expressed at a lower level in a second pool of libraries.

Transcript Imaging lists all of the clones in a single library or a pool of libraries based on abundance. Individual clones can then be examined using Electronic Northerns, to determine the tissue sources of their component ESTs.

Protein Function: Incyte has identified subsets of ESTs with a potential protein function based on homologies to known proteins. Some examples in this database include Transcription Factors and Proteases. Some leads were identified by searching in this database for clones whose component ESTs showed disease specificity.

Electronic subtractions, transcript imaging and protein function searches were used to identify clones, whose component ESTs were exclusively or more frequently found in libraries from specific tumors. Individual candidate clones were examined in detail by checking where each EST originated.

TABLE 1

LSGs

| SEQ ID # | Clone ID | Gene ID | Method |
|---|---|---|---|
| 1 | 2589190 | 6361 | Transcript Imaging |
| 2 | 1237018 | 6997 | Transcript Imaging |
| 3 | 1510111 | 5658 | Transcript Imaging |
| 4 | 1355520 | 236760 | Transcript Imaging |
| 5 | 3117390 | 7387 | Transcript Imaging |

The following example was carried out using standard techniques, which are well known and routine to those of skill in the art, except where otherwise described in detail. Routine molecular biology techniques of the following example can be carried out as described in standard laboratory manuals, such as Sambrook et al., MOLECULAR CLONING: A LABORATORY MANUAL, 2nd Ed.; Cold Spring Harbor Laboratory Press, Cold Spring Harbor, N.Y. (1989).

Example 2

Relative Quantitation of Gene Expression

Real-Time quantitative PCR with fluorescent Taqman probes is a quantitation detection system utilizing the 5'-3' nuclease activity of Taq DNA polymerase. The method uses an internal fluorescent oligonucleotide probe (Taqman) labeled with a 5' reporter dye and a downstream, 3' quencher dye. During PCR, the 5'-3' nuclease activity of Taq DNA polymerase releases the reporter, whose fluorescence can then be detected by the laser detector of the Model 7700 Sequence Detection System (PE Applied Biosystems, Foster City, Calif., USA).

Amplification of an endogenous control is used to standardize the amount of sample RNA added to the reaction and normalize for Reverse Transcriptase (RT) efficiency. Either cyclophilin, glyceraldehyde-3-phosphate dehydrogenase (GAPDH) or 18S ribosomal RNA (rRNA) was used as this endogenous control. To calculate relative quantitation between all the samples studied, the target RNA levels for one sample were used as the basis for comparative results (calibrator). Quantitation relative to the "calibrator" can be obtained using the standard curve method or the comparative method (User Bulletin #2: ABI PRISM 7700 Sequence Detection System).

The tissue distribution and the level of the target gene were evaluated for every example in normal and cancer tissue. Total RNA was extracted from these tissues and corresponding matched adjacent tissues. Subsequently, first strand cDNA was prepared with reverse transcriptase and the polymerase chain reaction was done using primers and Taqman probe specific to each target gene. The results were analyzed using the ABI PRISM 7700 Sequence Detector. The absolute numbers are relative levels of expression of the target gene in a particular tissue compared to the calibrator tissue.

Comparative Examples

Similar mRNA expression analysis for genes coding for the diagnostic markers PSA (Prostate Specific Antigen) and PLA2 (Phospholipase A2) was performed for comparison. PSA is the only cancer screening marker available in clinical laboratories. When the panel of normal pooled tissues was analyzed, PSA was expressed at very high levels in prostate, with a very low expression in breast and testis. After analysis of more than 55 matching samples from 14 different tissues, the data corroborated the tissue specificity seen with normal tissue samples. PSA expression was compared in cancer and normal adjacent tissue for 12 matching samples of prostate tissue. The relative levels of PSA were higher in 10 cancer samples (83%). Clinical data recently obtained support the utilization of PLA2 as a staging marker for late stages of prostate cancer. mRNA expression data showed overexpression of the mRNA in 8 out of the 12 prostate matching samples analyzed (66%). The tissue specificity for PLA2 was not as good as the one described for PSA. In addition to prostate, small intestine, liver, and pancreas also showed high levels of mRNA expression for PLA2.

Measurement of SEQ ID NO:5; Clone ID3117390; Gene ID7387 (Lng109)

The absolute numbers shown in Table 2 are relative levels of expression of Lng109 (SEQ ID NO5) in 12 normal different tissues. All the values are compared to normal small intestine (calibrator). These RNA samples are commercially available pools, originated by pooling samples of a particular tissue from different individuals.

TABLE 2

Relative levels of Lng109 Expression in Pooled Samples

| Tissue | NORMAL |
|---|---|
| Brain | 26.6 |
| Heart | 0.004 |
| Kidney | 0.016 |
| Liver | 0 |
| Lung | 46.6 |
| Mammary Gland | 0.2 |
| Muscle | 0.1 |
| Prostate | 0.4 |
| Small | 1 |
| Testis | 12.1 |
| Thymus | 0.2 |
| Uterus | 0.2 |

The relative levels of expression in Table 2 show that Lng109 (SEQ ID NO:5) mRNA expression is higher (46.6)

in lung compared with all the other normal tissues analyzed. Testis, with a relative expression level of 12.1, and brain (26.6) are the only other tissues expressing considerable mRNA for Lng109. These results establish that Lng109 mRNA expression is highly specific for lung.

The absolute numbers in Table 2 were obtained analyzing pools of samples of a particular tissue from different individuals. They can not be compared to the absolute numbers originated from RNA obtained from tissue samples of a single individual in Table 3.

The absolute numbers depicted in Table 3 are relative levels of expression of Lng109 (SEQ ID NO:5) in 57 pairs of matching samples. All the values are compared to normal small intestine (calibrator). A matching pair is formed by mRNA from the cancer sample for a particular tissue and mRNA from the normal adjacent sample for that same tissue from the same individual.

TABLE 3

Relative levels of Lng109 Expression in Individual Samples

| Sample ID | Cancer type | Tissue | Cancer | Matching Normal |
|---|---|---|---|---|
| LNG AC82 | Adenocarcinoma | Lung 1 | 16.6 | 0.9 |
| LNG 60XL | Adenocarcinoma | Lung 2 | 20.4 | 45.3 |
| LNG AC66 | Adenocarcinoma | Lung 3 | 12.4 | 7.5 |
| LNG AC69 | Adenocarcinoma | Lung 4 | 177.9 | 4.2 |
| LNG AC88 | Adenocarcinoma | Lung 5 | 89 | 33.7 |
| LNG AC11 | Adenocarcinoma | Lung 6 | 20.3 | 88.3 |
| LNG AC39 | Adenocarcinoma | Lung 7 | 103.3 | 1.8 |
| LNG AC90 | Adenocarcinoma | Lung 8 | 342.5 | 0.9 |
| LNG AC32 | Adenocarcinoma | Lung 9 | 152.7 | 0 |
| LNG SQ9X | Squamous cell carcinoma | Lung 10 | 14.2 | 0.7 |
| LNG SQ45 | Squamous cell carcinoma | Lung 11 | 179.8 | 15.9 |
| LNG SQ56 | Squamous cell carcinoma | Lung 12 | 55.5 | 59.3 |
| LNG SQ32 | Squamous cell carcinoma | Lung 13 | 21.3 | 6.4 |
| LNG SQ80 | Squamous cell carcinoma | Lung 14 | 83 | 36 |
| LNG SQ16 | Squamous cell carcinoma | Lung 15 | 27.2 | 4.8 |
| LNG SQ79 | Squamous cell carcinoma | Lung 16 | 11.2 | 18 |
| LNG C20X | Squamous cell carcinoma | Lung 17 | 0.2 | 0.63 |
| LNG 47XQ | Squamous cell carcinoma | Lung 18 | 188.1 | 0 |
| LNG SQ44 | Squamous cell carcinoma | Lung 19 | 6.3 | 0.2 |
| LNG BR94 | Squamous cell carcinoma | Lung 20 | 12 | 0 |
| LNG 90X | Squamous cell carcinoma | Lung 21 | 7.6 | 3.6 |
| LNG LC71 | Large cell carcinoma | Lung 22 | 69.1 | 168.3 |
| LNG LC109 | Large cell carcinoma | Lung 23 | 11.8 | 250.7 |
| LNG 75XC | Metastatic from bone cancer | Lung 24 | 1.5 | 1.8 |
| LNG MT67 | Metastatic from renal cancer | Lung 25 | 3.1 | 2.7 |
| LNG MT71 | Metastatic from melanoma | Lung 26 | 9.9 | 21.9 |
| BLD 32XK | | Bladder 1 | 0.1 | 0 |
| BLD 46XK | | Bladder 2 | 0.3 | 0 |
| CLN AS67 | | Colon 1 | 0.2 | 0.1 |
| CLN C9XR | | Colon 2 | 0.02 | 0 |
| CVX KS52 | | Cervix 1 | 0.1 | 0 |
| CVX NK23 | | Cervix 2 | 0.1 | 0 |

TABLE 3-continued

Relative levels of Lng109 Expression in Individual Samples

| Sample ID | Cancer type | Tissue | Cancer | Matching Normal |
|---|---|---|---|---|
| END 28XA | | Endometrium 1 | 2.2 | 0.1 |
| ENDO 12XA | | Endometrium 2 | 0 | 0 |
| ENDO 68X | | Endometrium 3 | 1.33 | 2.6 |
| ENDO 8XA | | Endometrium 4 | 0 | 0 |
| KID 106XD | | Kidney 1 | 0.1 | 0.1 |
| KID 109XD | | Kidney 2 | 0.1 | 0.2 |
| LIV 94XA | | Liver 1 | 0 | 0.04 |
| LIV 15XA | | Liver 2 | 48.6 | 0.03 |
| MAM A06X | | Mammary 1 | 0 | 0 |
| MAM 59X | | Mammary 2 | 0.9 | 0 |
| OVR 103X | | Ovary 1 | 0.5 | 2.6 |
| PAN 71XL | | Pancreas 1 | 0.1 | 0.1 |
| PAN 77X | | Pancreas 2 | 0.1 | 0 |
| PRO 20XB | | Prostate 1 | 0.3 | 0.1 |
| PRO 12B | | Prostate 2 | 0.3 | 0 |
| PRO 69XB | | Prostate 3 | 0.6 | 0.5 |
| SMI 21XA | | Sm. Int. 1 | 0.3 | 0 |
| SMI H89 | | Sm. Int. 2 | 0.1 | 0.2 |
| STO AC44 | | Stomach 1 | 0.2 | 0.2 |
| STO AC99 | | Stomach 2 | 0.1 | 0.2 |
| STO MT54 | | Stomach 3 | 0.3 | 0 |
| STO TA73 | | Stomach 4 | 0.4 | 0.7 |
| TST 39X | | Testis | 4.8 | 0.8 |
| UTR 135X0 | | Uterus 1 | 0.6 | 0.5 |
| UTR 141XO | | Uterus 2 | 0 | 0.1 |

0 = negative

In the analysis of matching samples, the higher levels of expression were in lung, showing a high degree of tissue specificity for lung tissue. Of all the samples different than lung analyzed, only one sample (the cancer sample Liver 2 with 48.6) showed an expression comparable to the mRNA expression in lung. These results confirmed the tissue specificity results obtained with the panel of normal pooled samples (Table 2).

Furthermore, the level of mRNA expression in cancer samples and the isogenic normal adjacent tissue from the same individual was compared. This comparison provides an indication of specificity for the cancer stage (e.g. higher levels of mRNA expression in the cancer sample compared to the normal adjacent). Table 3 shows overexpression of Lng109 in 16 primary lung cancer tissues compared with their respective normal adjacent (lung samples #1, 3, 4, 5, 7, 8, 9, 10, 11, 13, 14, 15, 18, 19, 20, and 21). There was overexpression in the cancer tissue for 70% of the lung matching samples tested (total of 23 lung matching samples).

Altogether, the high level of tissue specificity, plus the mRNA overexpression in 70% of the primary lung matching samples tested are demonstrative of Lng109 being a diagnostic marker for lung cancer.

Measurement of SEQ ID NO:4; Clone ID1355520 (1981752); Gene ID236760 (Lng110)

The absolute numbers depicted in Table 4 are relative levels of expression of Lng110 in 12 normal different tissues. All the values are compared to normal testis (calibrator). These RNA samples are commercially available pools, originated by pooling samples of a particular tissue from different individuals.

TABLE 4

Relative levels of Lng109 Expression in Pooled Samples

| Tissue | NORMAL |
| --- | --- |
| Brain | 0 |
| Heart | 0.003 |
| Kidney | 0.02 |
| Liver | 0 |
| Lung | 392.1 |
| Mammary | 0 |
| Muscle | 0 |
| Prostate | 0.1 |
| Sm. Int. | 0 |
| Testis | 1 |
| Thymus | 0.6 |
| Uterus | 0 |

The relative levels of expression in Table 4 show that Lng110 mRNA expression is more than 300 fold higher in the pool of normal lung (392.1) compared to all the other tissues analyzed. These results demonstrate that Lng110 mRNA expression is highly specific for lung.

The absolute numbers in Table 4 were obtained analyzing pools of samples of a particular tissue from different individuals. They can not be compared to the absolute numbers originated from RNA obtained from tissue samples of a single individual in Table 5.

The absolute numbers depicted in Table 5 are relative levels of expression of Lng110 in 60 pairs of matching samples. All the values are compared to normal testis (calibrator). A matching pair is formed by mRNA from the cancer sample for a particular tissue and mRNA from the normal adjacent sample for that same tissue from the same individual.

TABLE 5

Relative levels of Lng109 Expression in Individual Samples

| Sample ID | Cancer type | Tissue | Cancer | Matching Normal |
| --- | --- | --- | --- | --- |
| LNG AC82 | Adenocarcinoma | Lung 1 | 30.8 | 17 |
| LNG 60XL | Adenocarcinoma | Lung 2 | 18.2 | 40.1 |
| LNG AC66 | Adenocarcinoma | Lung 3 | 0 | 31.1 |
| LNG AC69 | Adenocarcinoma | Lung 4 | 44.8 | 5.3 |
| LNG AC88 | Adenocarcinoma | Lung 5 | 239.7 | 78.5 |
| LNG AC11 | Adenocarcinoma | Lung 6 | 10.7 | 1.3 |
| LNG AC39 | Adenocarcinoma | Lung 7 | 134.4 | 0.7 |
| LNG AC90 | Adenocarcinoma | Lung 8 | 373.5 | 4.6 |
| LNG AC32 | Adenocarcinoma | Lung 9 | 65.8 | 1.2 |
| LNG SQ9X | Squamous cell carcinoma | Lung 10 | 76.6 | 0.2 |
| LNG SQ45 | Squamous cell carcinoma | Lung 11 | 21.4 | 105.8 |
| LNG SQ56 | Squamous cell carcinoma | Lung 12 | 48.2 | 1049.1 |
| LNG SQ14 | Squamous cell carcinoma | Lung 13 | 2.3 | 0.7 |
| LNG SQ32 | Squamous cell carcinoma | Lung 14 | 3.2 | 0.5 |
| LNG SQ80 | Squamous cell carcinoma | Lung 15 | 191.3 | 0.3 |
| LNG SQ16 | Squamous cell carcinoma | Lung 16 | 21.3 | 0.7 |
| LNG SQ79 | Squamous cell carcinoma | Lung 17 | 1992 | 7.8 |
| LNG C20X | Squamous cell carcinoma | Lung 18 | 0.7 | 0.4 |
| LNG 47XQ | Squamous cell carcinoma | Lung 19 | 4.3 | 0 |
| LNG SQ44 | Squamous cell carcinoma | Lung 20 | 0 | 0 |
| LNG BR94 | Squamous cell carcinoma | Lung 21 | 100.8 | 0 |
| LNG 90X | Squamous cell carcinoma | Lung 22 | 5.2 | 45.4 |
| LNG LC71 | Large cell carcinoma | Lung 23 | 4.6 | 2.5 |
| LNG LC109 | Large cell carcinoma | Lung 24 | 876.1 | 111.4 |
| LNG 75XC | Metastatic from bone cancer | Lung 25 | 19 | 27.2 |
| LNG MT67 | Metastatic from renal cancer | Lung 26 | 0 | 0 |
| LNG MT71 | Metastatic from melanoma | Lung 27 | 0 | 5.2 |
| BLD 32XK |  | Bladder 1 | 0 | 0 |
| BLD 46XK |  | Bladder 2 | 0 | 0 |
| CLN AS67 |  | Colon 1 | 0 | 0 |
| CLN C9XR |  | Colon 2 | 0 | 0 |
| CLN CM67 |  | Colon 3 | 0 | 0 |
| CVX KS52 |  | Cervix 1 | 1.4 | 0 |
| CVX NK23 |  | Cervix 2 | 0 | 0 |
| CVX NKS18 |  | Cervix 3 | 0 | 0 |
| END 28XA |  | Endometrium 1 | 0.8 | 0 |
| ENDO 12XA |  | Endometrium 2 | 0 | 0 |
| KID 106XD |  | Kidney 1 | 0 | 0 |
| KID 107XD |  | Kidney 2 | 0 | 0 |
| KID 10XD |  | Kidney 3 | 0 | 0 |
| KID 11XD |  | Kidney 4 | 0 | 0 |
| LIV 94XA |  | Liver 1 | 0 | 0 |
| LIV 15XA |  | Liver 2 | 0 | 0 |
| MAM A06X |  | Mammary 1 | 0 | 0 |
| MAM B011X |  | Mammary 2 | 0 | 0 |
| MAM 12X |  | Mammary 3 | 0 | 0 |
| MAM 59X |  | Mammary 4 | 0 | 0 |
| OVR 103X |  | Ovary 1 | 0.1 | 0 |
| PAN 71XL |  | Pancreas 1 | 0 | 0 |
| PAN 77X |  | Pancreas 2 | 0 | 0 |
| PRO 20XB |  | Prostate 1 | 0 | 0 |
| PRO 12B |  | Prostate 2 | 0 | 0 |
| SMI 21XA |  | Small Intestine 1 | 0 | 0 |
| SMI H89 |  | Small Intestine 2 | 0 | 0 |
| STO AC44 |  | Stomach 1 | 0 | 0 |
| STO AC99 |  | Stomach 2 | 0 | 0 |
| TST 39X |  | Testis | 4.4 | 0 |
| UTR 135X0 |  | Uterus 1 | 0 | 0 |
| UTR 141X0 |  | Uterus 2 | 0 | 0 |

0 = negative

In the analysis of matching samples, the higher levels of expression were in lung showing a high degree of tissue specificity for lung tissue. These results confirm the tissue specificity results obtained with normal pooled samples (Table 4).

Furthermore, the level of mRNA expression in cancer samples and the isogenic normal adjacent tissue from the same individual was compared. This comparison provides an indication of specificity for the cancer stage (e.g. higher levels of mRNA expression in the cancer sample compared to the normal adjacent). Table 5 shows overexpression of Lng110 in 18 primary lung cancer samples compared with their respective normal adjacent (lung samples #1, 4, 5, 6, 7, 8, 9, 10, 13, 14, 15, 16, 17, 18, 20 19, 21, 23 and 24). There is overexpression in the cancer tissue for 75% of the lung matching samples tested (total of 24 primary lung matching samples).

Altogether, the high level of tissue specificity, plus the mRNA overexpression in 75% of the lung matching samples tested are demonstrative of Lng110 being a diagnostic marker for lung cancer. The amino acid sequence encoded by the open reading frame of Lng110 is depicted in SEQ ID NO:6.

What is claimed is:

1. An antibody which specifically binds to a protein encoded by a polynucleotide which comprises SEQ ID NO:5, said antibody detectably labeled or conjugated to a cytotoxic agent.

2. A method of imaging lung cancer in a patient comprising administering to the patient the detectably labeled antibody of claim 1, and measuring an amount of detectably labeled antibody within the lung to determine the presence or absence of cancer in the lung or to determine the location of cancer in the lung.

3. The method of claim 2 wherein said antibody is labeled with paramagnetic ions or a radioisotope.

* * * * *

SEQUENCE LISTING

<160> NUMBER OF SEQ ID NOS: 6

<210> SEQ ID NO 1
<211> LENGTH: 174
<212> TYPE: DNA
<213> ORGANISM: Homo sapien

<400> SEQUENCE: 1

| cataattggg | catactgtaa | tattctcaga | gatctatatg | taaaatttgt | atagtcatag | 60 |
| ttttatggtg | ggttataatt | gtctctagta | gattctgtga | gtctaaaaca | ataggaagac | 120 |
| tgtgctccat | tagcttgtca | tgcaattttt | aactttgaca | atagactttt | tttg | 174 |

<210> SEQ ID NO 2
<211> LENGTH: 276
<212> TYPE: DNA
<213> ORGANISM: Homo sapien

<400> SEQUENCE: 2

| aagaggagtc | tggaggtagg | gtccaagggc | cacgagccag | tttgggctgc | tggaggggg | 60 |
| cctggcaagg | agggctctcg | gggaagcacc | tgtgggggtc | tgcttcctga | ccccaggag | 120 |
| ctagaggcct | ccctccctcc | aggccccca | agccaggctg | agccagccgc | tagggcacg | 180 |
| gagcagtgcc | caccttgcgc | ccagtgtggc | cagagcttcg | gccggaagga | gctcagtgcg | 240 |
| ccgcaccagc | gcgtgcatcg | tggccccgg | cctttc | | | 276 |

<210> SEQ ID NO 3
<211> LENGTH: 347
<212> TYPE: DNA
<213> ORGANISM: Homo sapien
<220> FEATURE:
<221> NAME/KEY: misc_feature
<222> LOCATION: (279)..(280)
<223> OTHER INFORMATION: n=a, c, g, or t
<220> FEATURE:
<221> NAME/KEY: misc_feature
<222> LOCATION: (282)..(282)
<223> OTHER INFORMATION: n=a, c, g, or t
<220> FEATURE:
<221> NAME/KEY: misc_feature
<222> LOCATION: (311)..(311)
<223> OTHER INFORMATION: n=a, c, g, or t

<400> SEQUENCE: 3

| gttagcttca | caccttcggc | agcaggaggg | cggcagcttc | tcgcaggcgg | cagggcgggc | 60 |
| ggccaggatc | atgtccacca | ccacatgcca | agtggtggcg | ttcctcctgt | ccatcctggg | 120 |
| gctggccggc | tgcatcgcgg | ccaccgggat | ggacatgtgg | agcacccagg | acctgtacga | 180 |
| caaccccgtc | acctccgtgt | tccagtacga | agggctctgg | aggagctgcg | tgaggcagag | 240 |
| ttcaggcttc | accgaatgca | ggccctattt | caccatccnn | gnacttccag | ccatgctgca | 300 |
| ggcagtgcga | nccctgatga | tcgtaggcat | cgtcctgggt | gccattg | | 347 |

<210> SEQ ID NO 4
<211> LENGTH: 1016
<212> TYPE: DNA
<213> ORGANISM: Homo sapien

<400> SEQUENCE: 4

| | | | | | |
|---|---|---|---|---|---|
| acgggagag | agaggagacc | aggacagctg | ctgagacctc | taagaagtcc | agatactaag | 60 |
| agcaaagatg | tttcaaactg | ggggcctcat | tgtcttctac | gggctgttag | cccagaccat | 120 |
| ggcccagttt | ggaggcctgc | ccgtgcccct | ggaccagacc | ctgcccttga | atgtgaatcc | 180 |
| agccctgccc | ttgagtccca | caggtcttgc | aggaagcttg | acaaatgccc | tcagcaatgg | 240 |
| cctgctgtct | gggggcctgt | tgggcattct | ggaaaacctt | ccgctcctgg | acatcctgaa | 300 |
| gcctggagga | gtacttctg | gtggcctcct | tgggggactg | cttggaaaag | tgacgtcagt | 360 |
| gattcctggc | ctgaacaaca | tcattgacat | aaaggtcact | gaccccccagc | tgctggaact | 420 |
| tggccttgtg | cagagccctg | atggccaccg | tctctatgtc | accatccctc | tcggcataaa | 480 |
| gctccaagtg | aatacgcccc | tggtcggtgc | aagtctgttg | aggctggctg | tgaagctgga | 540 |
| catcactgca | gaaatcttag | ctgtgagaga | taagcaggag | aggatccacc | tggtccttgg | 600 |
| tgactgcacc | cattcccctg | gaagcctgca | aatttctctg | cttgatggac | ttggcccct | 660 |
| ccccattcaa | ggtcttctgg | acagcctcac | agggatcttg | aataaagtcc | tgcctgagtt | 720 |
| ggttcagggc | aacgtgtgcc | ctctggtcaa | tgaggttctc | agaggcttgg | acatcaccct | 780 |
| ggtgcatgac | attgttaaca | tgctgatcca | cggactacag | tttgtcatca | aggtctaagc | 840 |
| cttccaggaa | ggggctggcc | tctgctgagc | tgcttcccag | tgctcacaga | tggctggccc | 900 |
| atgtgctgga | agatgacaca | gttgccttct | ctccgaggaa | cctgcccct | ctcctttccc | 960 |
| accaggcgtg | tgtaacatcc | catgtgcctc | acctaataaa | atggctcttc | ttctgc | 1016 |

<210> SEQ ID NO 5
<211> LENGTH: 597
<212> TYPE: DNA
<213> ORGANISM: Homo sapien

<400> SEQUENCE: 5

| | | | | | |
|---|---|---|---|---|---|
| tggctcgtga | gtcccttggg | catcccgctc | ctgggcaggt | caccaatagg | tccccgcagt | 60 |
| tcccaatgga | actgttccag | tcctccccga | ggcctccact | tcaacctgtc | tgtgtctgcc | 120 |
| caggcctgga | gttgtgtgac | cctccccacc | gcctggcctt | ctccatgggg | gctggccttt | 180 |
| tctcggtggt | gggcaccctg | ctgctgcccg | gcctggctgc | gcttgtgcag | gactggcgtc | 240 |
| ttctgcaggg | gctgggtgcc | ctgatgagtg | gactcttgct | gctctttttgg | gggaggaggt | 300 |
| ggagggagcc | gtgggcatcc | tcaccaacgc | tgcaggttcc | cggccctgtt | ccccgagtct | 360 |
| ccctgctggc | tgctggccac | aggtcaggta | gctcgagcca | ggaagatcct | gtggcgcttt | 420 |
| gcagaagcca | gtgcgtggg | ccccggggac | agttccttgg | aggagaactc | cctggctaca | 480 |
| gagctgacca | tgctgtctgc | acggagcccc | cagccccggt | accactcccc | actgggcttt | 540 |
| ctgcgtaccc | gagtcacctg | gagaaacggg | cttatcttgg | gcttcagctc | gctggtt | 597 |

<210> SEQ ID NO 6
<211> LENGTH: 256
<212> TYPE: PRT
<213> ORGANISM: Homo sapien

<400> SEQUENCE: 6

Met Phe Gln Thr Gly Gly Leu Ile Val Phe Tyr Gly Leu Leu Ala Gln

-continued

```
  1               5                    10                   15
Thr Met Ala Gln Phe Gly Gly Leu Pro Val Pro Leu Asp Gln Thr Leu
            20                  25                  30

Pro Leu Asn Val Asn Pro Ala Leu Pro Leu Ser Pro Thr Gly Leu Ala
            35                  40                  45

Gly Ser Leu Thr Asn Ala Leu Ser Asn Gly Leu Leu Ser Gly Gly Leu
        50                  55                  60

Leu Gly Ile Leu Glu Asn Leu Pro Leu Leu Asp Ile Leu Lys Pro Gly
65                      70                  75                  80

Gly Gly Thr Ser Gly Gly Leu Leu Gly Gly Leu Leu Gly Lys Val Thr
                85                  90                  95

Ser Val Ile Pro Gly Leu Asn Asn Ile Ile Asp Ile Lys Val Thr Asp
                100                 105                 110

Pro Gln Leu Leu Glu Leu Gly Leu Val Gln Ser Pro Asp Gly His Arg
            115                 120                 125

Leu Tyr Val Thr Ile Pro Leu Gly Ile Lys Leu Gln Val Asn Thr Pro
        130                 135                 140

Leu Val Gly Ala Ser Leu Leu Arg Leu Ala Val Lys Leu Asp Ile Thr
145                 150                 155                 160

Ala Glu Ile Leu Ala Val Arg Asp Lys Gln Glu Arg Ile His Leu Val
                165                 170                 175

Leu Gly Asp Cys Thr His Ser Pro Gly Ser Leu Gln Ile Ser Leu Leu
            180                 185                 190

Asp Gly Leu Gly Pro Leu Pro Ile Gln Gly Leu Leu Asp Ser Leu Thr
            195                 200                 205

Gly Ile Leu Asn Lys Val Leu Pro Glu Leu Val Gln Gly Asn Val Cys
        210                 215                 220

Pro Leu Val Asn Glu Val Leu Arg Gly Leu Asp Ile Thr Leu Val His
225                 230                 235                 240

Asp Ile Val Asn Met Leu Ile His Gly Leu Gln Phe Val Ile Lys Val
                245                 250                 255
```